United States Patent
McGovern et al.

(10) Patent No.: US 6,645,215 B1
(45) Date of Patent: Nov. 11, 2003

(54) TIBIAL ROTATION GUIDE

(75) Inventors: Michael A. McGovern, Wyckoff, NY (US); Richard Lackman, Abington, PA (US)

(73) Assignee: Howmedica Osteonics Corp., Allendale, NJ (US)

(*) Notice: Subject to any disclaimer, the term of this patent is extended or adjusted under 35 U.S.C. 154(b) by 0 days.

(21) Appl. No.: 10/213,715

(22) Filed: Aug. 7, 2002

(51) Int. Cl.$^7$ ............................................... A61B 17/58
(52) U.S. Cl. ......................................... 606/102; 606/88
(58) Field of Search ............................ 606/102, 86, 87, 606/88, 89, 80, 85, 96; 623/20.22, 20.23, 20.3, 20.33, 20.34

(56) References Cited

U.S. PATENT DOCUMENTS

| | | |
|---|---|---|
| 4,301,553 A | 11/1981 | Noiles |
| 6,063,091 A * | 5/2000 | Lombardo et al. ............ 606/88 |
| 6,228,091 B1 | 5/2001 | Lombardo et al. |
| 6,258,095 B1 | 7/2001 | Lombardo et al. |
| 6,355,045 B1 * | 3/2002 | Gundlapalli et al. .......... 606/88 |
| 2002/0082607 A1 * | 6/2002 | Heldreth et al. ............. 606/102 |
| 2003/0009228 A1 * | 1/2003 | Meyers et al. ............. 623/20.24 |
| 2003/0100953 A1 * | 5/2003 | Rosa et al. ................. 623/20.3 |

FOREIGN PATENT DOCUMENTS

EP          1 219 269 A1      7/2002

OTHER PUBLICATIONS

"Modular Rotating Hinge Knee System Using Monogram® IM Revision Instrument," Howie et al., Monogram® Total Knee Instruments, Howmedica Osteonics 2001, Lit. No. 64811083, pp. 1–24.

* cited by examiner

*Primary Examiner*—Pedro Philogene
*Assistant Examiner*—David A Bonderer
(74) *Attorney, Agent, or Firm*—Lerner, David, Littenberg, Krumholz & Mentlik, LLP

(57) ABSTRACT

An instrument for utilization in the rotational alignment of a hinged prosthetic knee implant has two selectively coupled parts for mounting on the tibia. The prosthetic knee implant has a tibial portion and a femoral portion. The femoral component has a hinged portion. The first part of the instrument is a trial tibial template for engaging the resected proximal tibia. The second part is a trial hinge component that has a portion for selectively coupling with the trial template in an orientation forming the tibial portion of the prosthetic knee implant. The trial hinge component has a hinge portion which selectively mates with the hinge on the femoral component. The rotational alignment of the tibial portion of the prosthetic knee implant may be determined by coupling the hinged portion of the trial hinge component to the hinge on the femoral component and moving the resected tibia throughout the range of motion desired and pinning the trial tibia template in the appropriate position on the resected tibia.

27 Claims, 16 Drawing Sheets

TIBIAL ROTATION GUIDE

BACKGROUND OF THE INVENTION

This invention relates to instrumentation for implanting a prosthetic hinged knee. More particularly, it relates to instrumentation for locating the internal/external rotation of the tibial component of the hinged knee on a resected tibia.

According to one preferred aspect of the present invention there is provided a total knee replacement prosthesis (TKR) which comprises a femoral component which is pivotably connected to a tibial component at a hinge for pivoting movement about a medial-lateral axis. One portion of the hinge is preferably formed on the femoral component. The preferred tibial hinge component is rotably received within a bearing component adapted to be mounted on a tibial baseplate having a stem implanted in the tibial intramedullary canal, so that the tibial hinge component is rotatable within the bearing component to provide a degree of internal/external rotational freedom of movement for the prosthesis. The preferred femoral component includes a stem portion for implantation within the canal of the femur.

In general, the tibial and femoral components are constructed from a metal which is biomedically inert, e.g. a stainless steel, a cobalt-chromium-molybdenum alloy such as Vitallium® alloy or a titanium alloy. The bearing components should preferably exhibit low friction with respect to the component which rotates within them and typically materials which meet this requirement are polyolefines. Particularly, preferred materials for this purposes are ultra-high molecular weight polyethylenes. Preferably, the rotational movement takes place by rotation of a tibial stem within a tubular or hollow bearing component which is fixed relatively to the tibia. Thus, for example, the tibial hinge component may comprise a distally facing surface with a stem portion extending distally and a hinge portion for connection to the femoral component at its proximal end. At the distal end the stem is received in the bearing component with the distally facing surface rotating on the proximal bearing surface. The tibial baseplate component may have an internal bore dimensioned to receive the tibial hinge component stem and an external surface suitably sized to fit the tibial bone canal.

In a preferred embodiment, the tibial and femoral components are pivotably connected by a hinge. Such a hinge has a pin or axle which passes through aligned bores in the two components. In the preferred embodiment, each condyle of the femoral component includes a hinge part and the tibial component includes a centrally located hinge part extending within the intra-condylar notch of the femoral component. Bushings may be used in the bores of the hinge parts for improved wear and reduced friction. These bushings may be made of plastic such as ultra-high molecular weight polyethylene. Alternatively, the femoral component may include a body portion which has a bore to receive the hinge pin and the tibial component may include a pair of ears or lugs which extend on each side of the body portion of the femoral component. The hinge pin or axle is preferably removably fixed by suitable locking means, such as circlips in apertures in the hinge parts. Thus, the femoral and tibial components can be installed in their relative intramedullary canals and the joint made by introducing the hinge pin and the locking means.

Such a prosthetic hinge knee joint is taught in U.S. Pat. No. 4,301,553, the teachings of which are incorporated herein by reference. With this hinged knee design as well as many later designs, there has been a need to facilitate the rotational alignment of the tibial and femoral components with respect to the patients anatomy so that once the hinge pin is inserted between the femoral component and the tibial components and the components fixed to the distal femur and proximal tibia, the soft tissue balance produces a natural gate after implantation.

Often a modular rotating hinged knee system is designed for knees with severe joint destruction and/or ligament instability where a condylar style non-hinged implant is not appropriate. While the hinge mechanism has been designed for those knees in which the soft tissue envelope is compromised, where possible, the collateral ligaments should be preserved to enhance the longevity of the device. In order to accomplish this, the proper tension of the knee must be maintained by the soft tissue, thus requiring a trial reduction to ensure correction of the alignment instability along with an estimation of the range of motion of the prosthesis after implantation.

Currently, there is a need for a method of determining the optimal rotational orientation of the tibial baseplate of a hinged knee prosthesis prior to its permanent implantation on the proximal tibia. There has particularly been a need for instrumentation which would allow the surgeon to set the internal/external rotation of the foot and optimize the patellar tracking along the femoral component before the tibia is resurfaced.

U.S. Pat. Nos. 6,228,091 and 6,258,095 disclose methods and instruments for resecting the distal femur and proximal tibia in a manner similar described herein. The teachings of these patents are incorporated herein by reference. The tibial rotation guide of the present invention is intended to be used in a procedure similar to that described in U.S. Pat. No. 6,228,091 but tailored for use with a hinged knee prosthesis.

SUMMARY OF THE INVENTION

It is an object of the invention to provide an instrument which allows the determination of the correct internal/external rotation of the tibial component after the location and implantation of a femoral component or a femoral trial has been accomplished.

It is an additional object of the invention to provide an instrument which is capable of locating the proper internal/external rotation of both the hinged tibial component and the hinged femoral component after the femoral component has been located on a prepared distal femur but prior to the location of the tibial component on a resected proximal tibia.

These and other objects of the invention are accomplished by a tibial rotation guide having two modular parts, the first part being a trial tibial template and the second part being a hinge part. The hinge part being removably coupled to the first part, and includes a hinge portion for coupling the trial tibial component to a hinged portion of the hinged femoral component. The two part tibial rotation guide is assembled and coupled to the hinged connection on the located femoral component allowing the surgeon to then place the previously resected proximal tibia flush against the underside of the tibial template. Joint space, range of motion, leg length and tissue balance can then be evaluated.

The tibial rotation guide includes a plurality of tibial templates and hinge parts which, when assembled with its mating components on the femur, mimic the various tibial baseplate insert thicknesses. Therefore, if the joint space between the femoral component and the tibial component of the prosthesis is not appropriate, the surgeon may select a different tibial rotation guide which represents the next available insert thickness and sizes. This step may be repeated until the appropriate joint space is achieved. In addition, various sizes of trial tibial templates are provided to correspond to various sizes of resected proximal tibias. A tibial alignment handle may also be assembled to the tibial template to help to verify alignment of the tibial axis in the medial-lateral and anterior-posterior planes. An alignment pin may extend from the alignment handle in a proximal-distal direction for alignment purposes. In addition, the patella may be placed back over the femoral component and while maintaining the proximal tibia flush against the underside of the template the tibia may be internally and externally rotated until optimal patella tracking is achieved in conjunction with the femoral component. The template is then fixed to the tibia and the joint can be flexed through its range of motion to further evaluate patella tracking. Finally, the hinged part of the tibial rotation guide can be disassembled from both the femoral component and the tibial template and tibial baseplate preparation can begin.

If it is desired to orient the femoral component rather than initially locating the femoral component on a fully prepared distal femur, the trial femoral component is inserted into the prepared femoral canal in a manner described hereinbelow which allows rotation with respect to the unprepared distal femur. The tibial rotation guide is then assembled as above and coupled to the hinge on the trial femoral component and the internal/external rotation of the femur and tibial component are set in a manner which optimizes patella tracking and range of motion.

BRIEF DESCRIPTION OF THE DRAWINGS

The invention can be performed in various ways and various embodiments will now be described by way of examples and with reference to the accompanying drawings in which.

DETAILED DESCRIPTION

Figure 1:
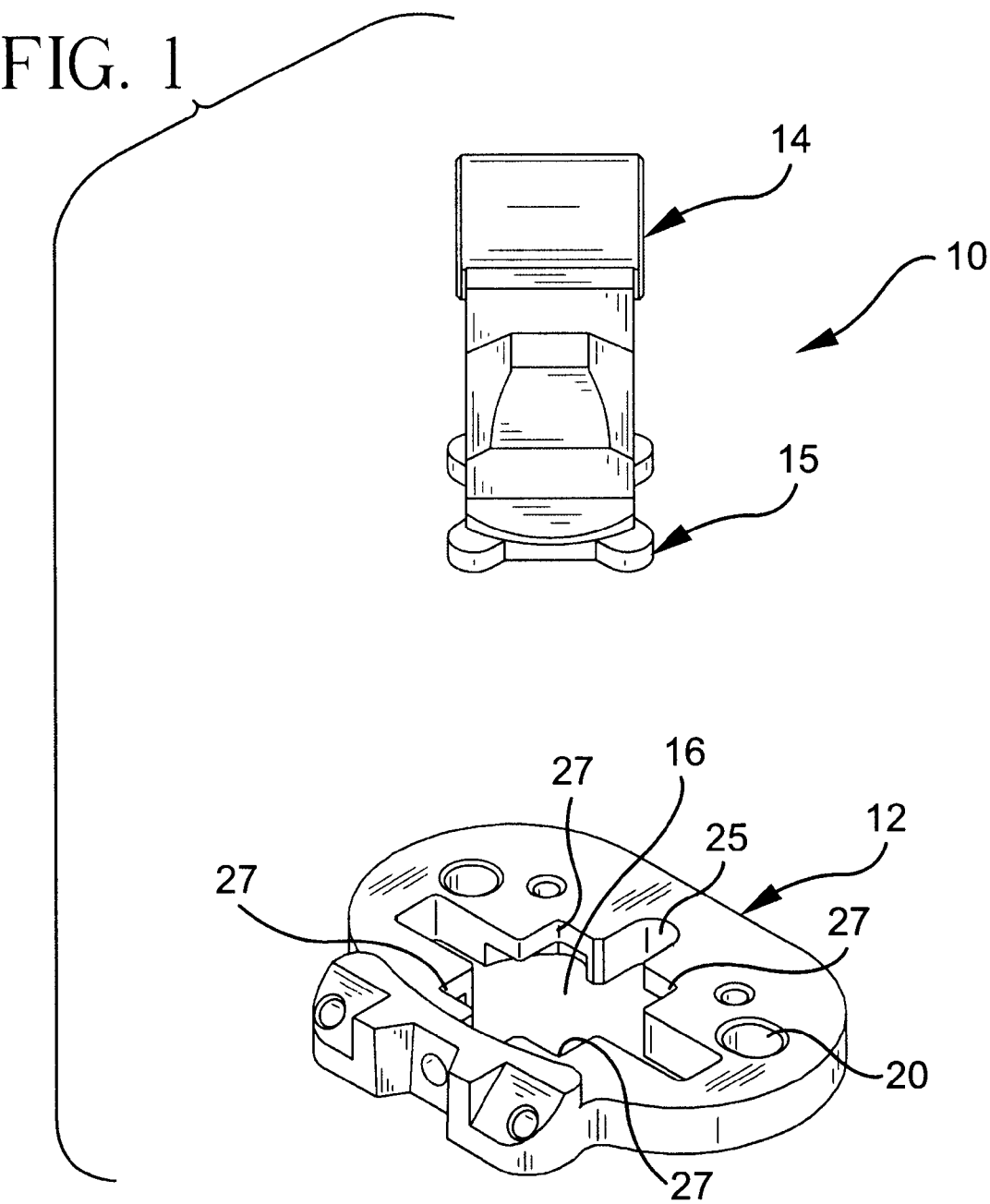
FIG. 1 is an exploded view of the tibial template and rotational alignment guide of the present invention.
Figure 2:
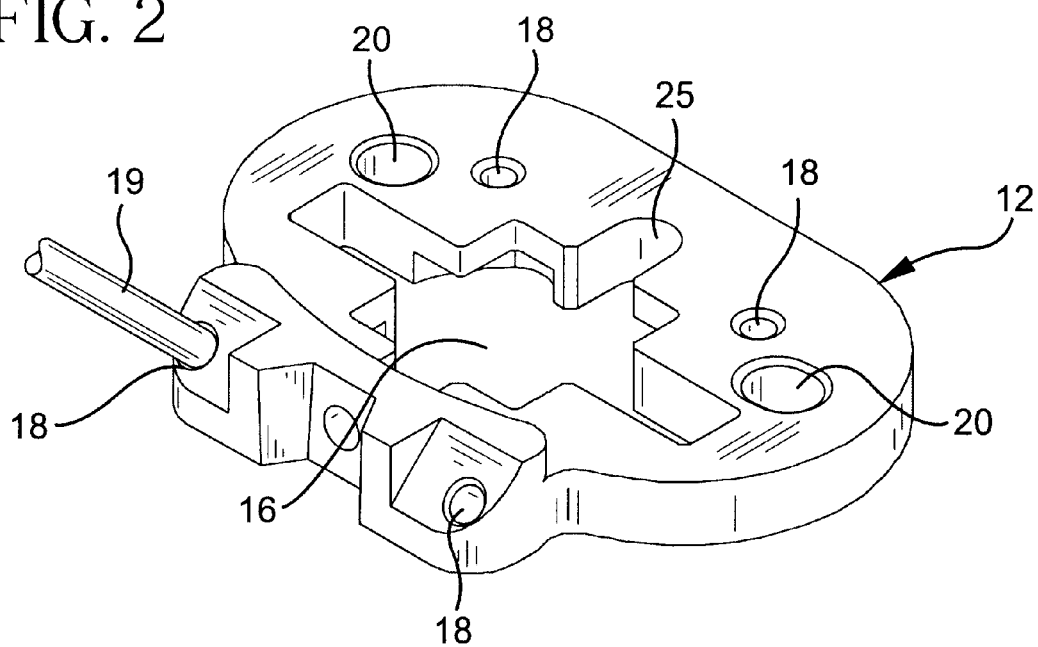
FIG. 2 is an isometric top view of the tibial template shown in FIG. 1.
Figure 3:
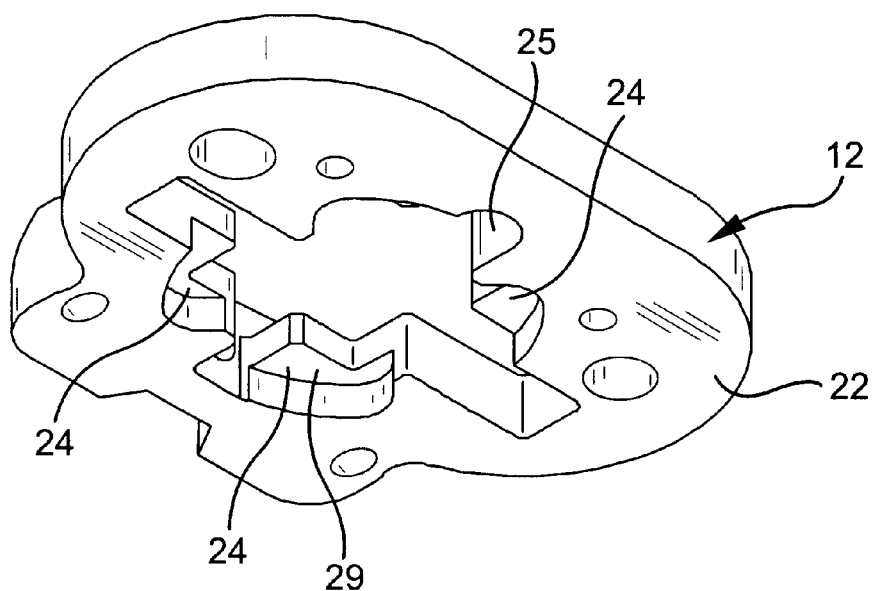
FIG. 3 is an isometric bottom view of the tibial template of FIG. 2.
Figure 4:
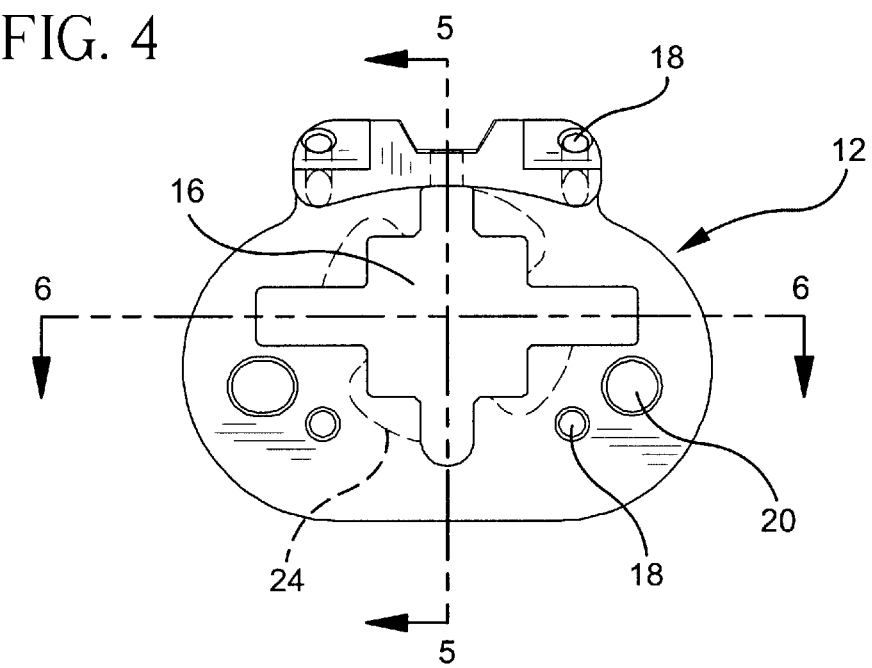
FIG. 4 is a plan view of the tibial template shown in FIGS. 1—3.
Figure 5:
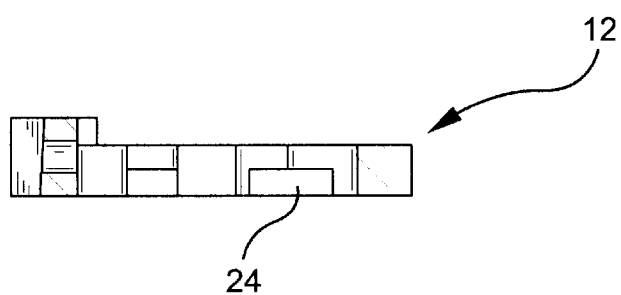
FIG. 5 is a cross-sectional view of the tibial template of FIG. 4 along lines 5—5.
Figure 6:
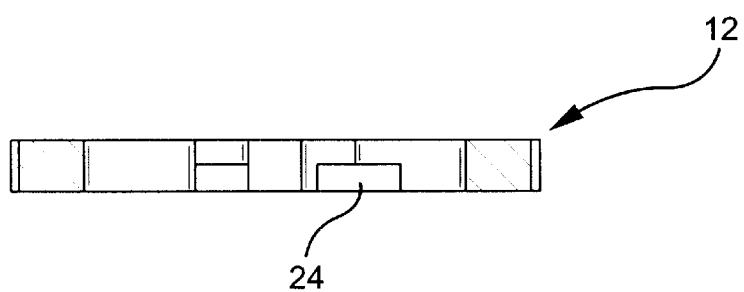
FIG. 6 is a cross-sectional view of the tibial template of FIG. 4 along lines 6—6.
Figure 7:
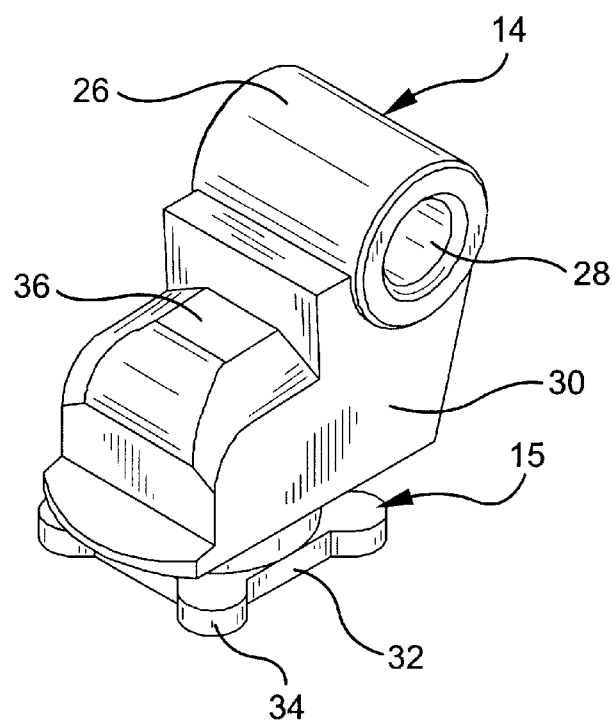
FIG. 7 is an isometric view of the tibial rotation guide of the present invention viewed from above.
Figure 8:
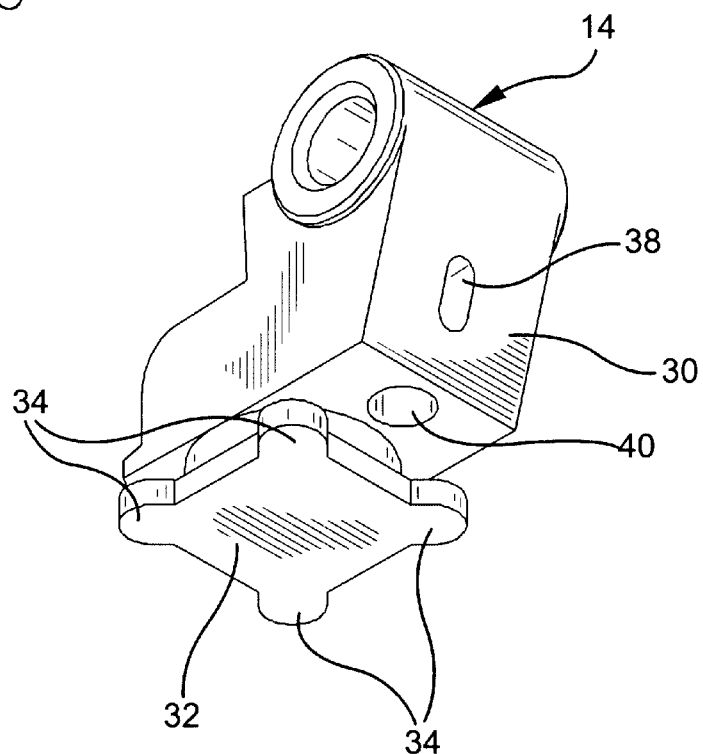
FIG. 8 is an isometric view of the tibial rotation guide of the present invention viewed in the direction in which it is assembled to the tibial template.
Figure 9:
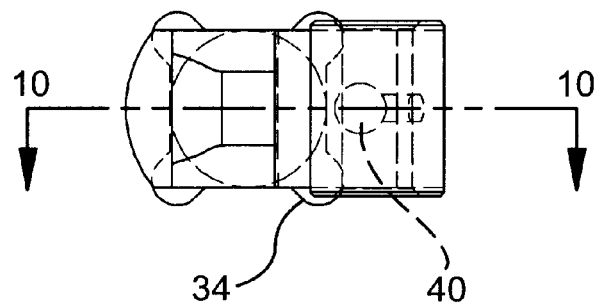
FIG. 9 is a plan view of the tibial rotation guide of FIG. 7.

Referring to FIG. 1, there is shown an isometric exploded view of the tibial rotation guide of the present invention generally denoted as 10. The tibial rotation guide 10 is composed of a tibial template 12 and a rotating hinge part 14. Referring to FIGS. 2–6, the tibial template 12 includes an opening 16 for receiving a distal end 15 of rotating hinge portion 14 as well as for receiving various instruments for preparing the resected tibia for receipt of a prosthetic tibial implant. This instrumentation will be discussed in more detail hereinbelow.

Tibial template 12 includes a plurality of pin holes 18 for temporarily coupling the tibial template 12 to a resected tibia via the use of pins 19 after proper alignment has been determined. The template 12 also includes openings 20 utilized for mounting various instruments on the template. In general, template 12 has the circumferential shape of a resected tibia and has a bone contacting surface 22 which includes a series of four curvilinear recess portions 24. Recess portions 24 are designed to rotatably engage distal end 15 of hinge part 14.

Referring to FIGS. 7–11, hinge part 14 of tibial rotation guide 10 includes a hinge portion 26 including a bore 28 extending from a body 30. Extending distally from the body 30 at distal end 15 is a coupling plate 32 which includes a plurality of feet 34. In the preferred embodiment, plate 32 includes four feet 34. Body 30 includes a bumper portion 36 intended to engage the femoral component positioned on the prepared distal femur. Bumper part 36 mimics a bumper on the mounted implanted prosthetic hinge element. It should be noted that a plurality of hinge parts 14 may be provided, each corresponding to the size of the rotating tibial hinge portion of the implanted prosthetic hinge knee joint. Various sized tibial hinge portions are required to adjust the distance between the tibial and the femur to provide the correct leg length. In this regard, hinge portions 26 of various heights are provided to accommodate various gaps corresponding to various polyethylene insert thicknesses. Typically, four or five different heights are provided simulating gaps of between about 8 and 24 mm.

Figure 10:
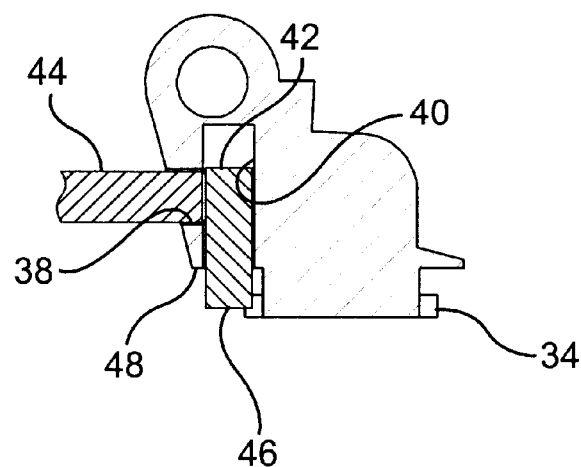
FIG. 10 is a cross-sectional view of the tibial rotation guide of FIG. 9 along lines 10—10.
Figure 11:
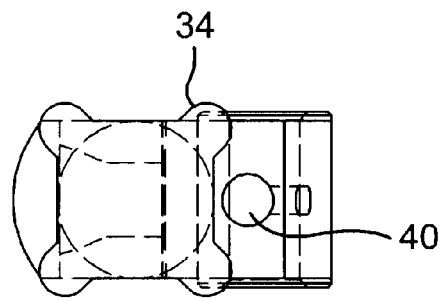
FIG. 11 is a bottom view of the tibial rotation guide of FIG. 8.

In the preferred embodiment, body 30 includes a first bore 38 extending in the anterior/posterior direction and a second bore 40 extending in a superior/inferior direction. Bores 38 and 40 intersect, with bore 40 designed to accommodate an anti-rotation pin 42 (FIG. 10) which is selectively engageable with a slot 25 in template 12. This engagement prevents the hinge portion from rotating out of engagement with the tibial baseplate once they are coupled. Bore 38 includes a pin 44 designed to engage pin 42 and hold it in position in bore 40 either engaged in slot 25 or out of engagement therewith. As can be seen in FIG. 10, bore 40 has a depth at least equal to the length of pin 42 so that an end 46 of pin 42 may be located generally flush with surface 48 of body 30.

Figure 12:
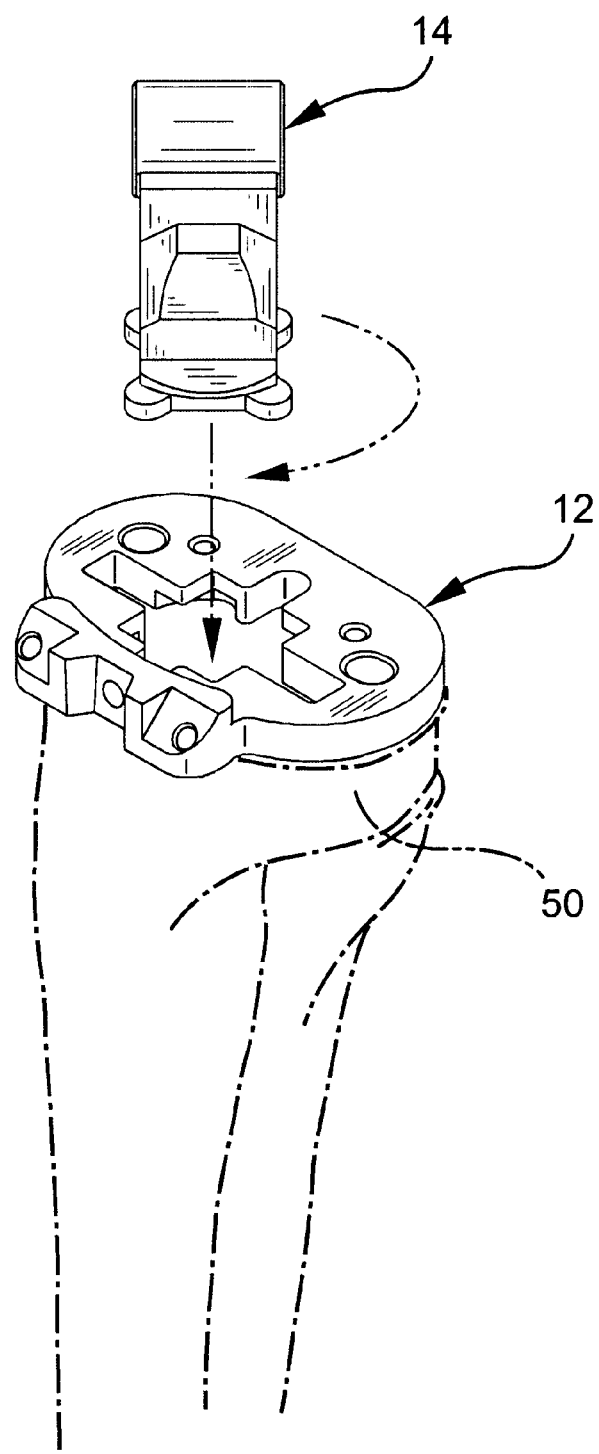
FIG. 12 is an exploded view showing the assembly of the tibial rotation guide onto a tibial template mounted on the proximal tibia.

Referring to FIG. 12, there is shown the assembly of hinge part 14 onto tibial template 12. Part 14 is moved downwardly into recess 16 with feet 34 aligned with corners 27 of template 12. Feet 34 are moved below surface 29 of template 12 and rotated into recesses 24. At this point, hinge part 14 is trapped against movement in the proximal/distal direction with respect to the tibia 50 since plate 32 is in contact with tibial bone on one side and surface 29 on the proximal side. Pin 42 can then engage slot 25 to prevent the hinge portion 14 from rotating with respect to tibia template 12. Although in the preferred embodiment, coupling of template 12 and hinge part 14 is done via plate 32 engaging recess 24, any other method for selectively releasably connecting the two parts could be used.

Figure 13:
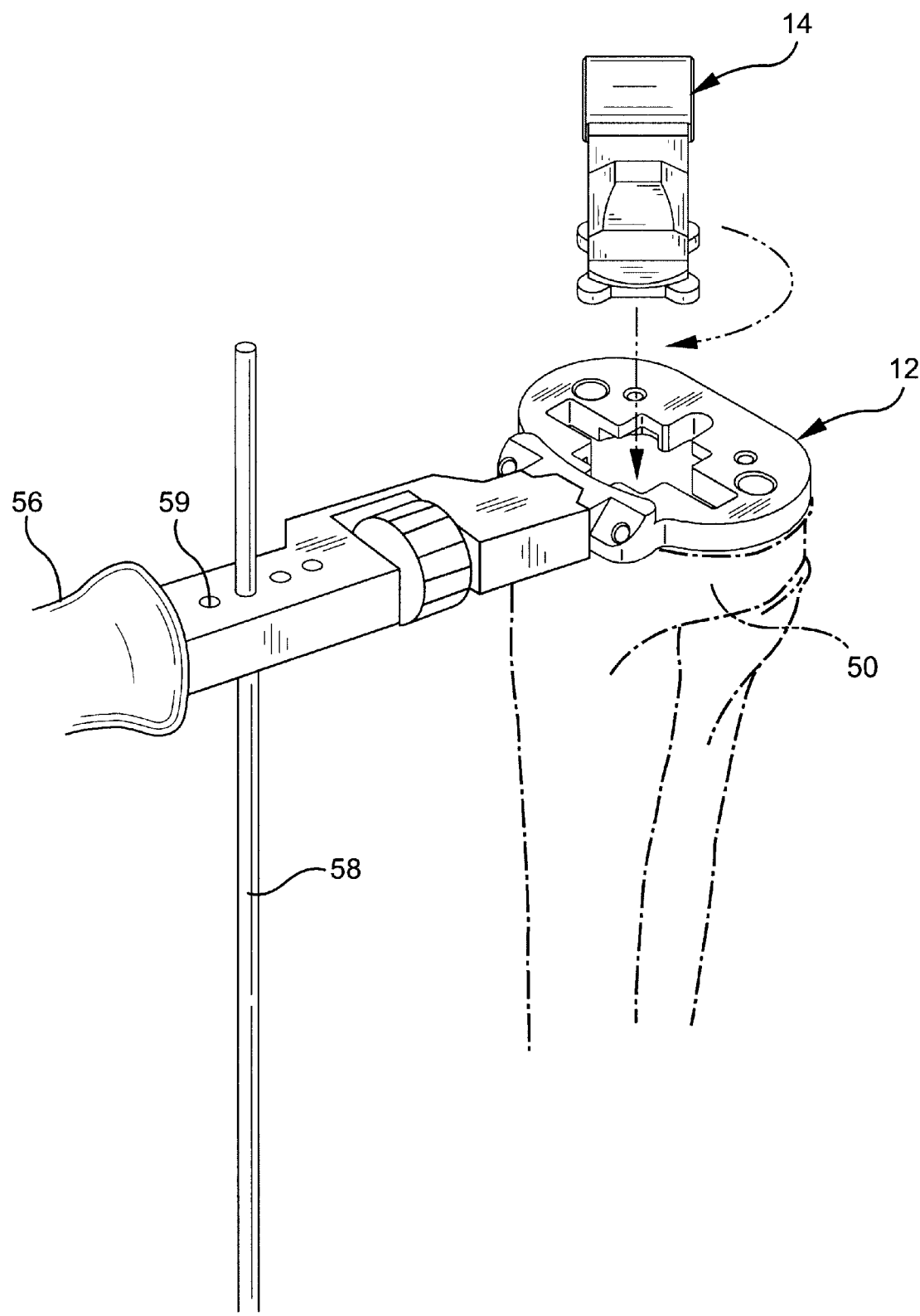
FIG. 13 shows the use of an alignment handle and guide rod in the alignment of the tibial template on the proximal tibia.
Figure 14:
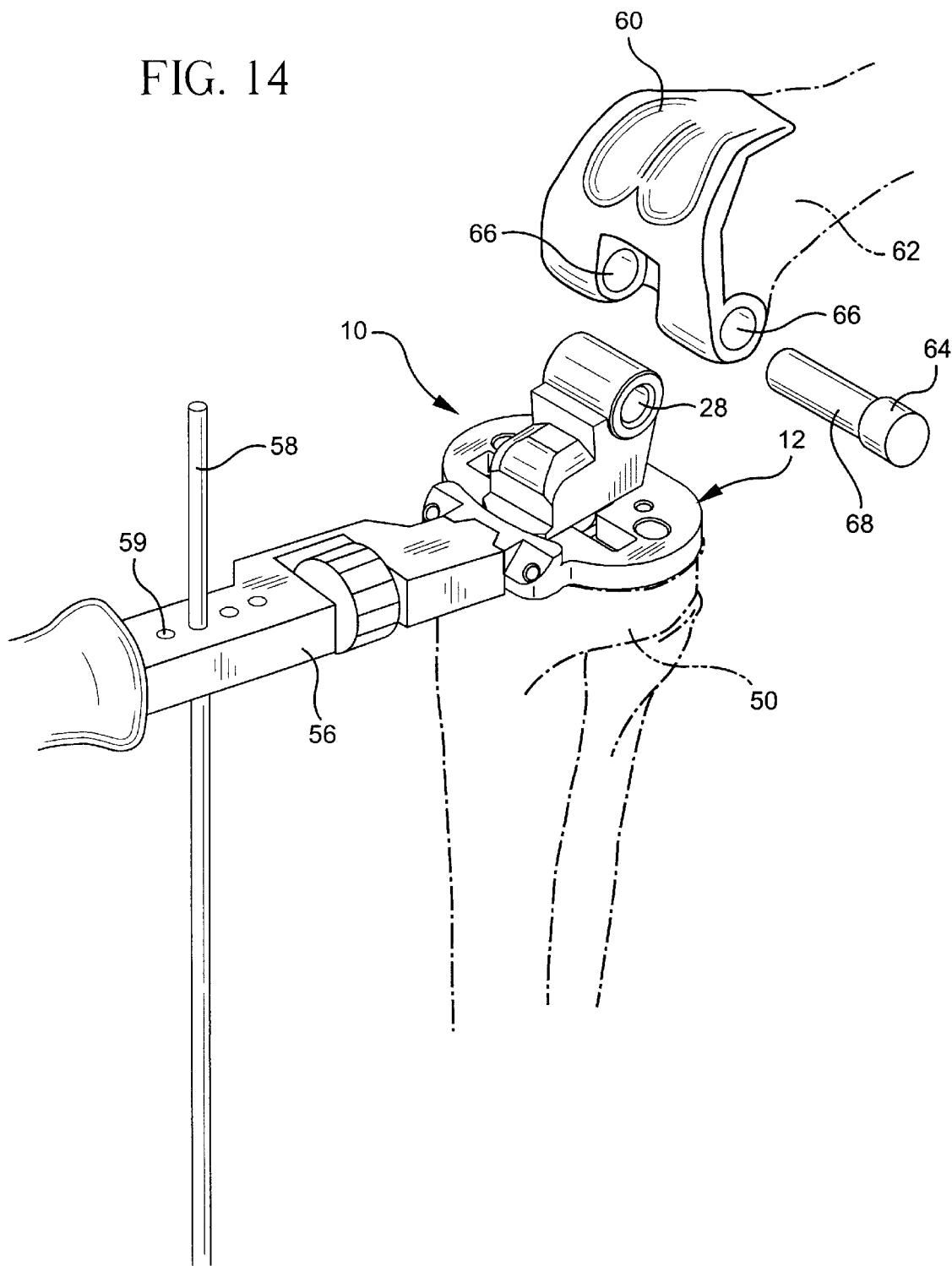
FIG. 14 is a view depicting the assembly of the tibial template rotational alignment guide combination within the hinge formed on a trial femur immediately prior to inserting the axle or hinge pin therein.

Referring to FIGS. 13 and 14, there is shown a tibial alignment handle 56 releasably coupled to template 12 in any convenient manner. In the preferred embodiment, handle 56 is threaded to template 12, however, a spring release such as a spring loaded clamp can also be used. The handle must be removed to allow the surgeon to evaluate the patellar tracking. Alignment handle 56 includes an alignment rod 58 which may be aligned with the axis of the tibia 50 in order to verify the varus/valgus and flexion/extension alignment of template 12. Handle 56 includes at least one hole and preferably four holes 59 for mounting rod 58. Holes 59 may be drilled in handle 56 at different angles to compensate for the cutting of the proximal tibial in a non-neutral angle, i.e. in a plane not perpendicular to the tibial axis such as when cutting the proximal tibia with a posterior slope. One of the holes 59 is in "neutral" alignment, i.e. perpendicular to the tibial axis in all planes. After evaluation of the plane of resection handle 56 is removed.

Referring to FIG. 14, there is shown the tibial rotation guide 10 with portion 12 and template 14 assembled. At this point, template 12 is not pinned to the resected proximal end of tibia 50. A trial or actual femoral component 60 is shown in position on a resected femur 62. Hinge pin or axle 64 is utilized to couple the hinged portions 66 on femoral component 60 with the hinge portion 26 of hinge part 14. The axle portion 68 is designed to slidably engage the hinge portion 66 of femoral component 60 and bore 28 of hinge portion 26. Once coupled together with hinge pin 64, the rotational guide 10 is rotated about the generally planar resected proximal end of tibia 15 as the surgeon manipulates the tibia over its range of motion to ensure correct internal/external rotational alignment.

Referring to FIGS. 15–19, there are shown stem preparation instruments being coupled to the tibial template 12 for preparation of the tibia. These instruments can be of any form and the instruments described are for illustrative purposes only.

Figure 15:
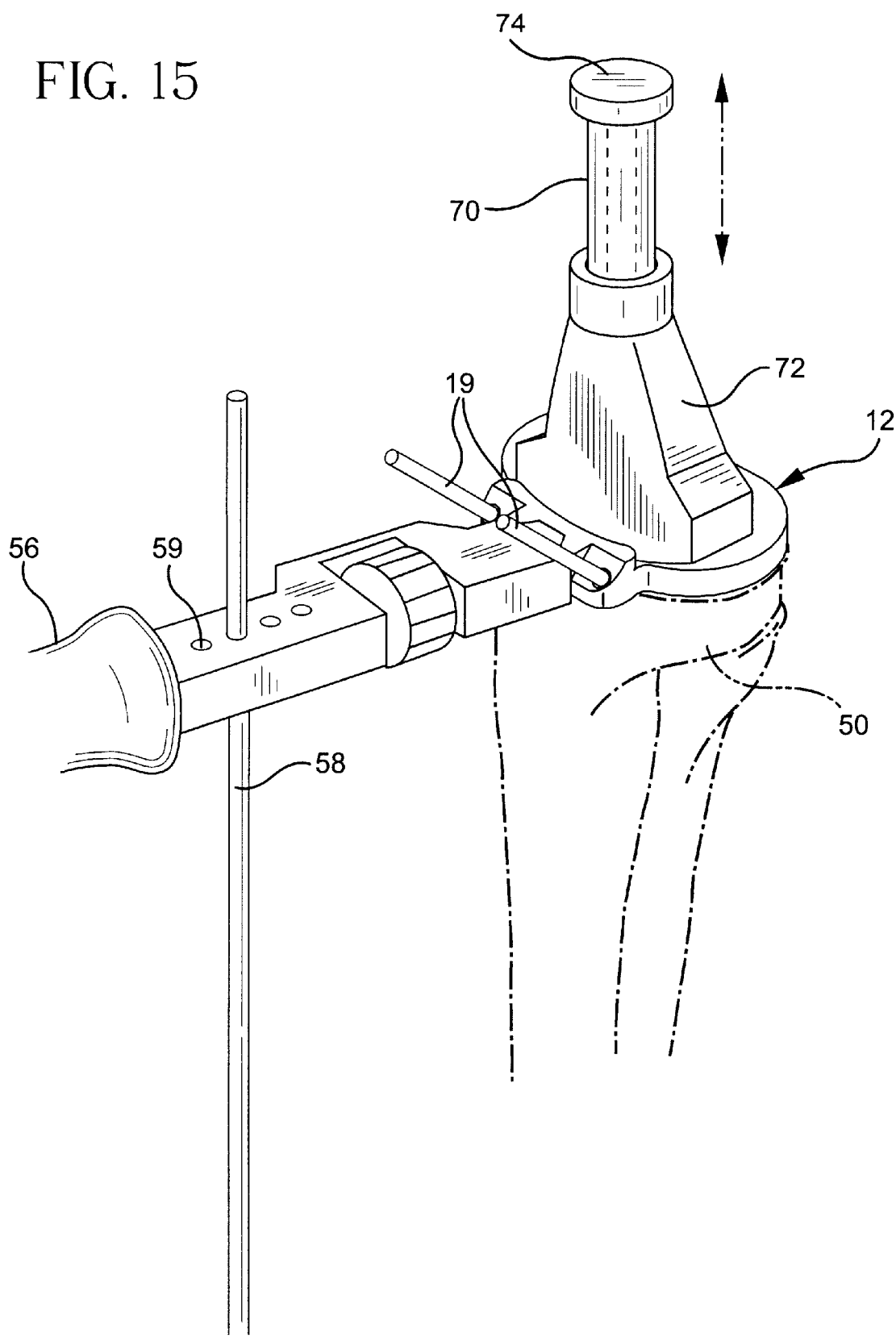
FIG. 15 is a view depicting the utilization of the tibial template mounted on the proximal tibia as a guide for a tibial stem recess forming tool.

Referring to FIG. 15, there is shown a stem punch 70 and stem punch guide 72 mounted on template 12 after template 12 has been pinned to tibia 50 with pins 19. The stem punch 70 is received within stem punch guide 72. A plunger 74 is inserted into a bore of stem punch 70 in order to position a bone plug (not shown) in the intramedullary canal of tibia 50.

Figure 16:
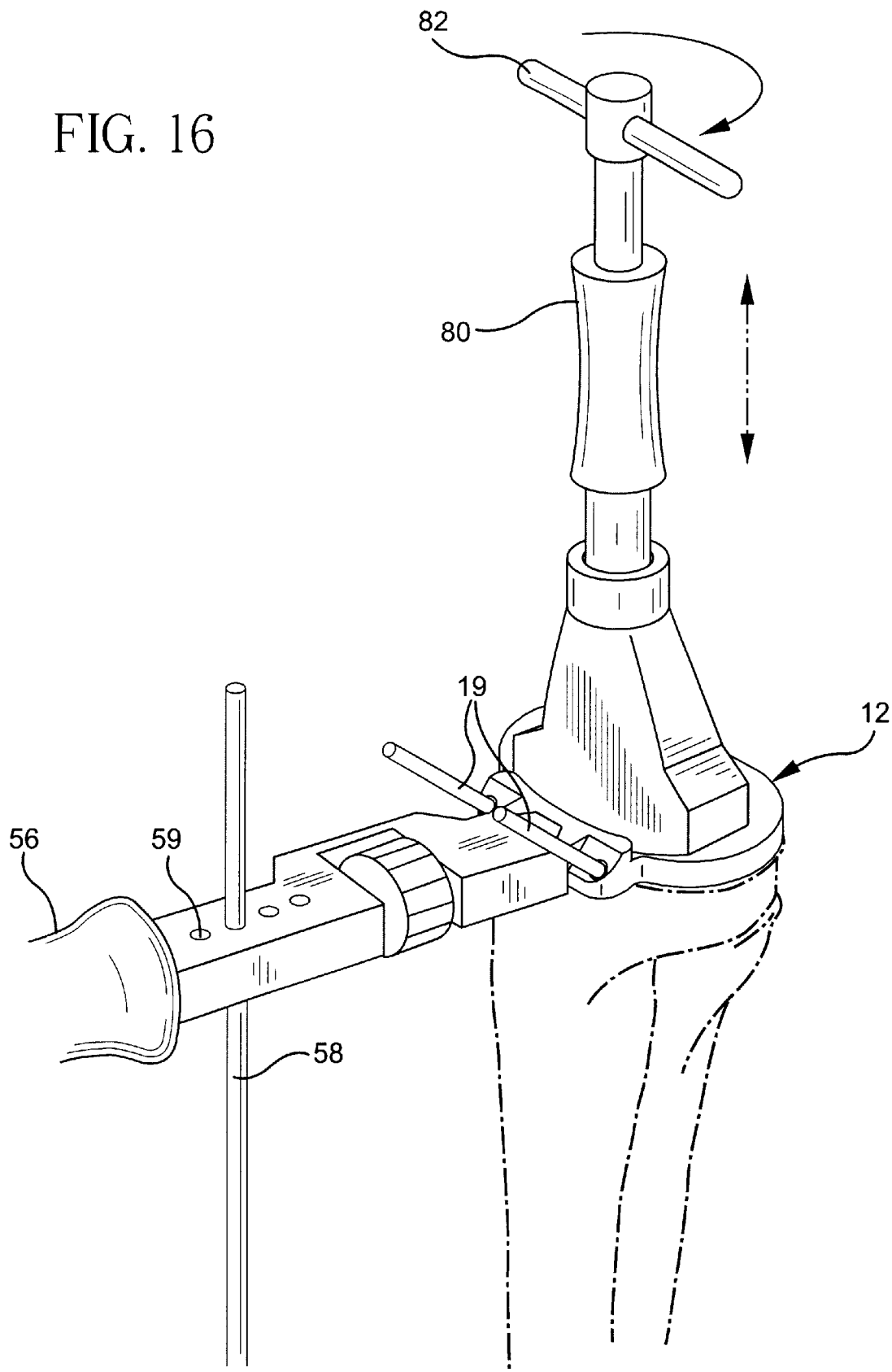

Referring to FIG. 16, there is shown an impactor/extractor 80 which drives the stem punch into the proximal tibia in order to form a recess for the stem of the implant. Handle 82 is provided to rotate the extractor. After the recess is formed the impactor/extractor can be used to remove the punch from the tibia.

Figure 17:
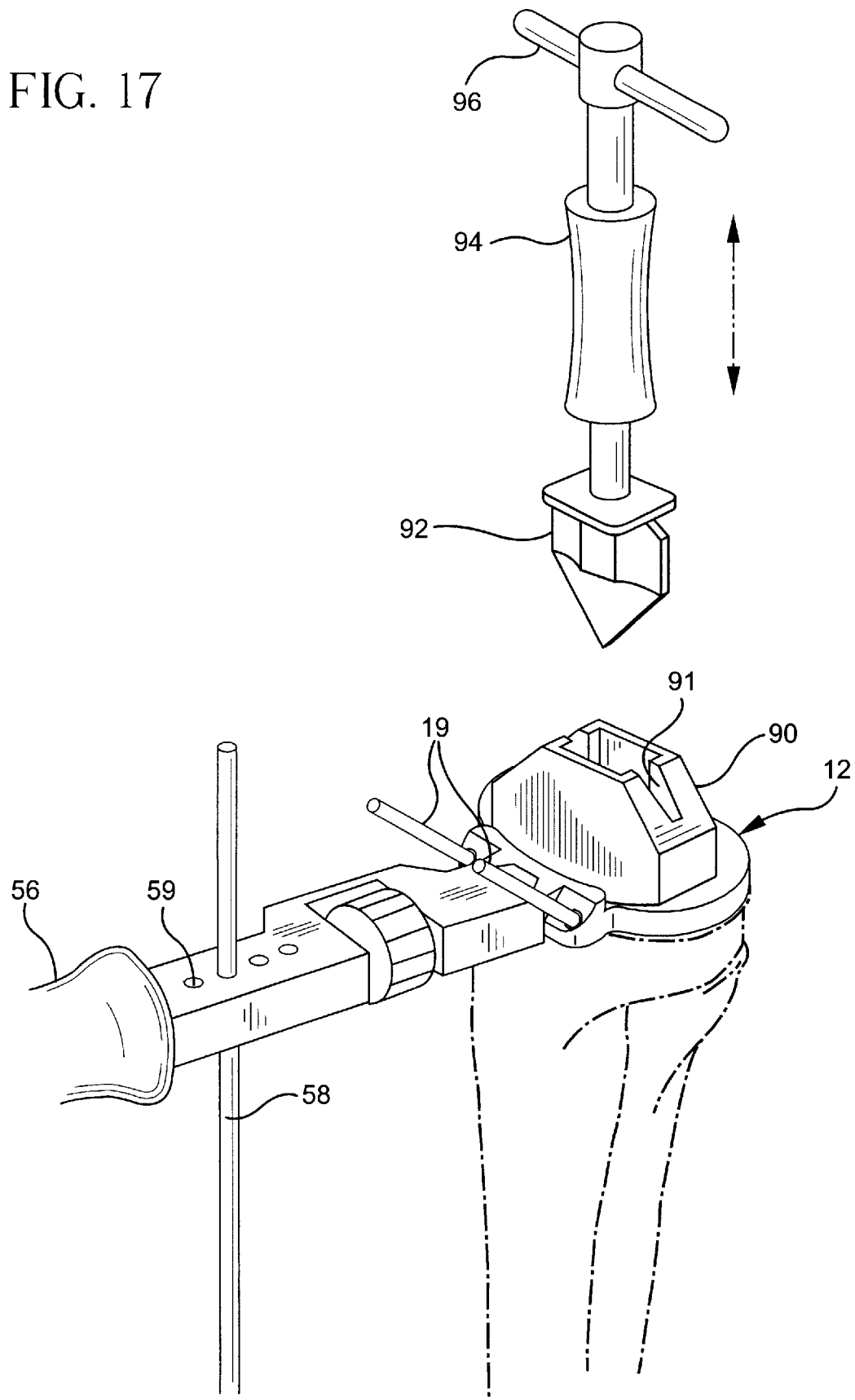
FIGS. 17–19 show various tools for use with the guide mounted on the tibial template for forming recesses in the tibia to accommodate the stem and/or rotation fins of standard tibial implants.

Referring to FIG. 17, there is shown a rectangular fin/box punch guide 90 mounted on template 12. Since the tibial implant (not shown) may include fins, a first thinner fin punch 92 is provided to form the initial recess for the fins. An extractor/impactor 94 with rotation handle 96 is provided to drive in the fin punch 92 and remove the same from the tibia.

Figure 18:
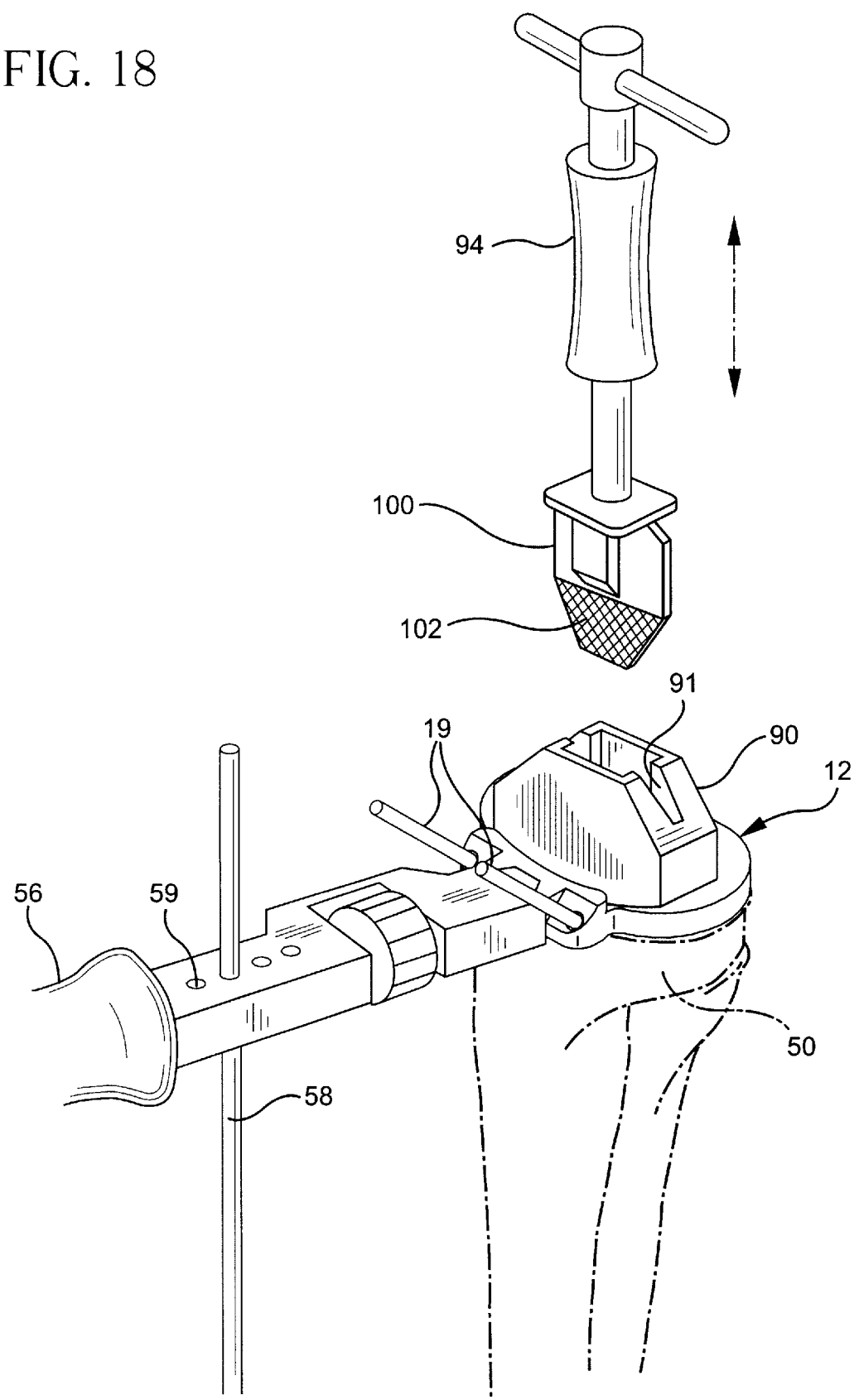

Referring to FIG. 18, a second thicker fin broach 100 is attached to the extractor/impactor 94. The thicker fin broach includes teeth 102 and is used to form the cavity for the stem fin within the proximal tibia. It has been found that forming the fin recess in two steps avoids excess deformation of bone which may result in damaging the tibia.

Figure 19:
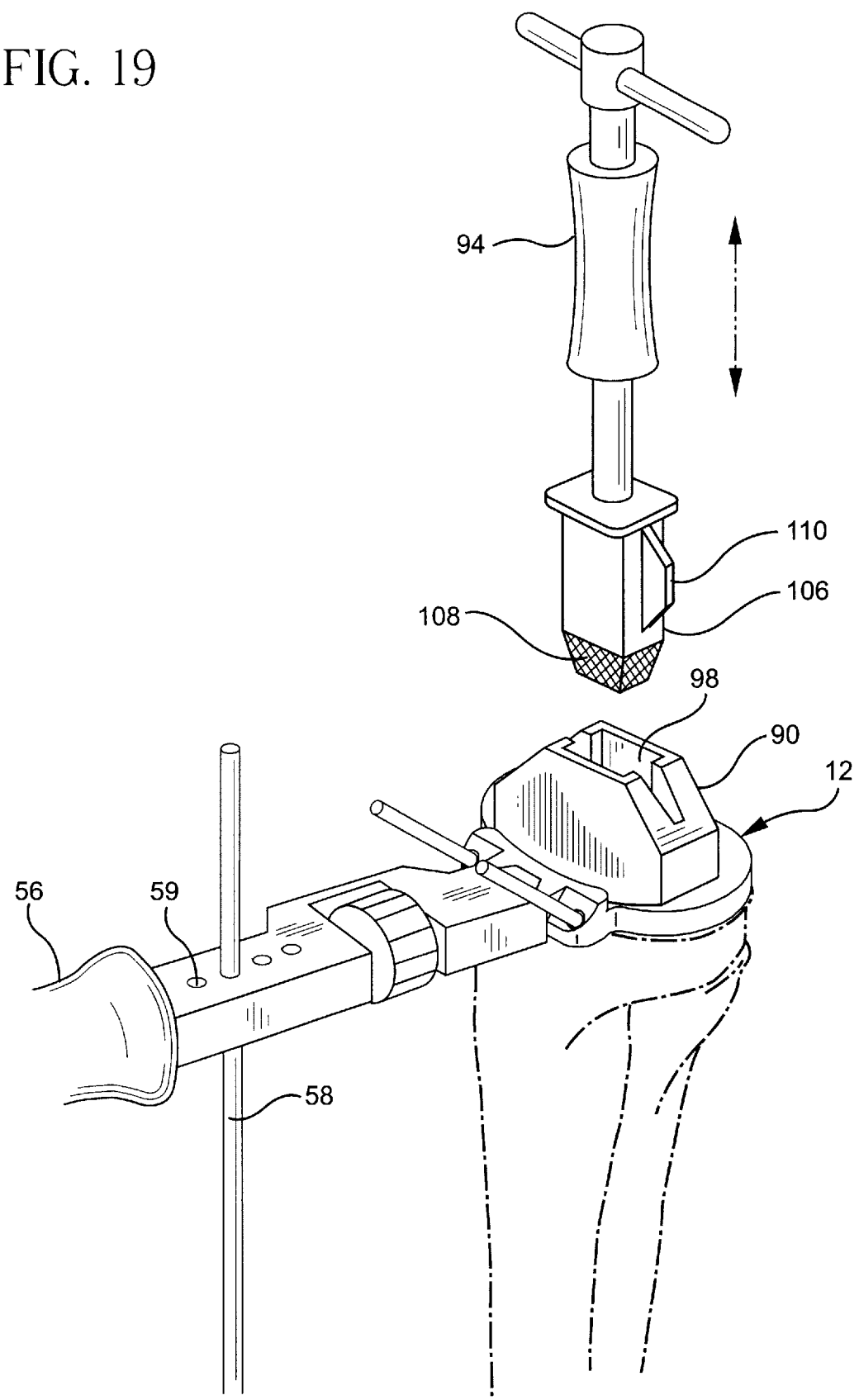

Referring to FIG. 19, there is shown a box broach 106 which is inserted within the rectangular opening 98 of rectangular fin/box punch guide 90. Box broach 106 includes teeth 108, a guide fin 110 and is attachable to the inserter/extractor 94. After the box is formed, the intramedullary canal of the proximal tibia 50 may be then opened to its final diameter to receive the stem of the prosthetic tibial implant by a standard reamer (not shown).

Figure 20:
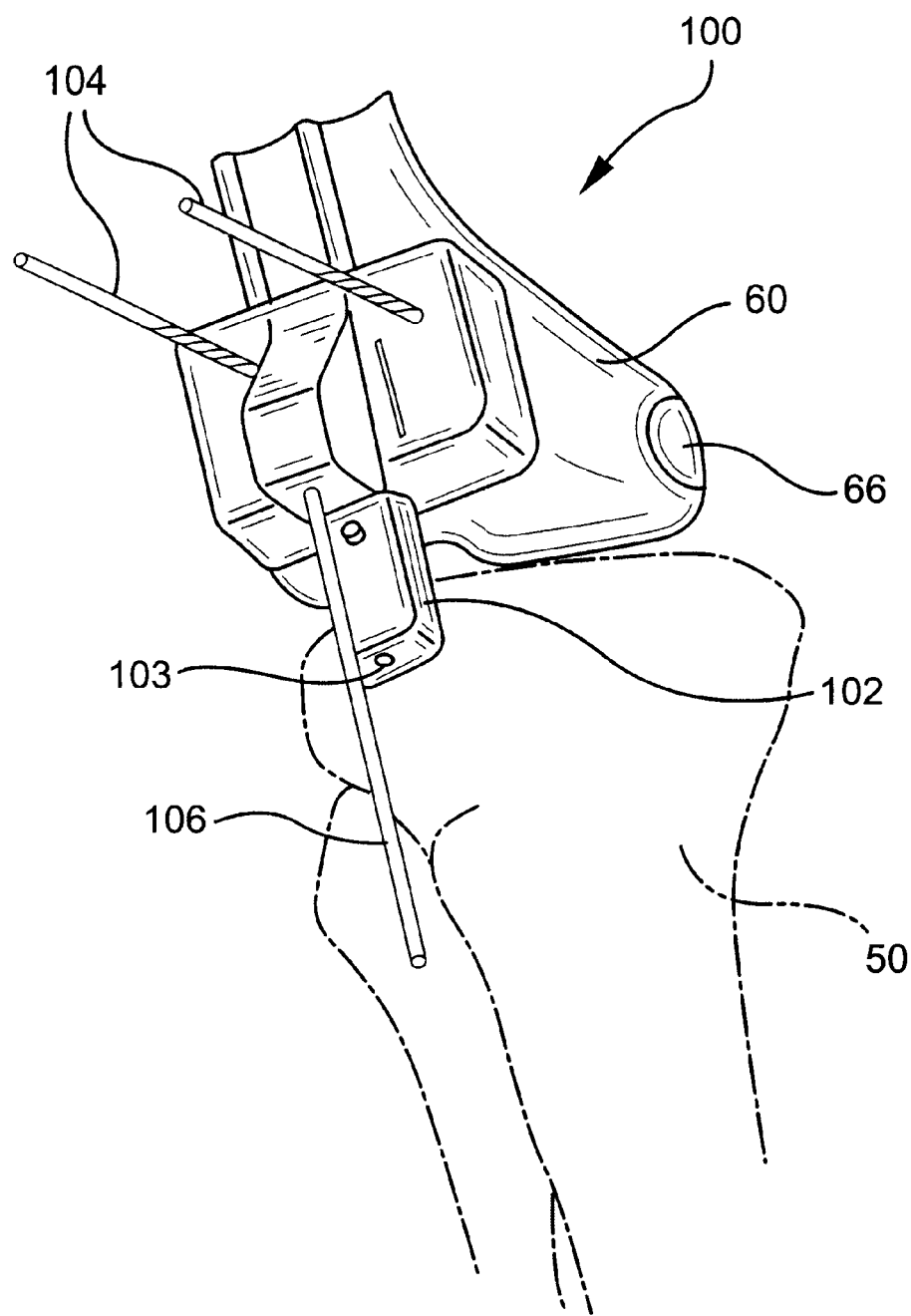
FIG. 20 is an isometric view of a tibial marking guide for determining the level of the resection of the tibia.

The following is a description of the surgical procedure used to prepare the proximal tibia with the instrumentation of the present invention. Usually the required initial proximal tibial resection is neutral to the tibial axis in all planes, i.e., cut in classical alignment with no posterior slope. The amount of bone to be removed, when taken into consideration with the femoral resection, will reconstruct the pre-operative joint line and leg length. The instrumentation provides two options for determining the resection level of the proximal tibia. Referring to FIG. 20 there is shown the first option which uses a tibial marking guide 100 to mark the tibial cut in relation to the femoral prosthesis or trial. A second option (not shown) utilizes a stylus to set the depth of the tibial cut.

It is important to note that if the condyles of the prosthesis are placed at the level of the pre-operative condyles (i.e., the femoral prosthesis makes up for the exact length of the resected femur). A longer tibial resection of about 17 mm could be required. Typically, a lesser tibial resection is desirable for example 10 mm. In this case it may be necessary to take additional resection of the femur. The femoral resection is therefore usually about 5 mm longer than the prosthesis.

Referring to FIG. 20, with the femoral trial prosthesis 60 in place, the tibial cut indicator 102 is attached to the femoral trial 60 with two pins, for example two ⅛-inch pins or drills 104. An alignment rod 106 is attached to cut indicator 102 to aid in aligning the tibia 50. The tibia 50 is gently distracted in line with the alignment rod with the appropriate amount of tension on the soft tissues.

The tibia 50 is marked at the level of the marking surface 103 on the tibial cut indicator 102 initially by setting the marking guide for the thinnest tibial component supplied. If the resection level will not remove any bone, the tibial cut indicator can be set for a thicker tibial component and then marked.

If the surgeon feels that too much tibia must be removed for the thinnest tibial component, additional bone can be removed from the femur. It is suggested that whenever additional bone is removed from the femur, the level of the patella is checked in reference to the prosthesis to ensure proper patellar tracking.

Once the level of the tibia cut has been marked along marking surface 103, either the extramedullary referencing or the intramedullary referencing instrumentation can be used to align the tibial cutting block. The depth of the cutting block is then set at the marked resection level.

There are two options for aligning the tibial cut: extramedullary referencing alignment and intramedullary referencing alignment.

Figure 21:
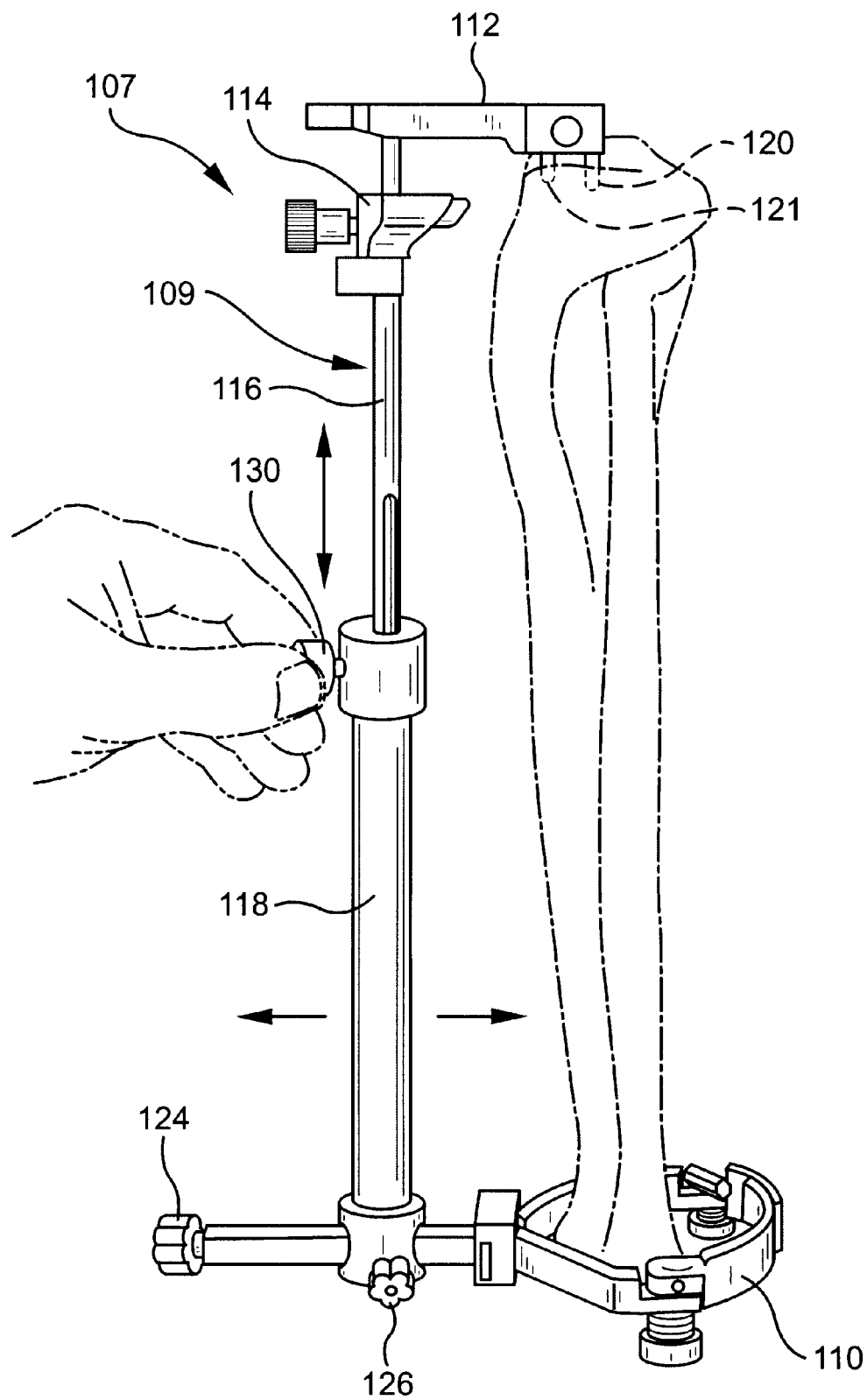
FIG. 21 is an elevation view of an extramedullary referencing apparatus for aligning a tibial cutting jig.

Referring to FIG. 21, there is shown an extramedullary referencing instrument 107. As shown in FIG. 21, the proximal tibial cutting assembly 109 has two parts, the ankle clamp 110 and the proximal alignment guide 112. Clamp 110 and guide 112 are assembled first. Guide 112 includes fixation pins 120 and 121. Then the tibial cutting jig 114 is positioned over the thin section 116 of the proximal guide assembly shaft 118, slid proximally, and locked into position.

The long fixation pin 120 of the proximal alignment guide 112 is partially seated in the proximal tibia to stabilize the assembly.

Flexion/extension alignment is correct when the long axis of the assembly parallels the midcoronal plane of the tibia. Flexion/extension alignment can be further confirmed by seeing that the long axis of the assembly is parallel to the fibula. Distal locking knob 124 is then tightened.

Medial/lateral offset can be adjusted using distal locking knob 126. The assembly 107 is slid medially until the jig shaft intersects the center of the tibia.

The whole assembly is fixed in place by striking the proximal end of the guide 112 with a mallet, securing the two fixation pins 120, 121. Once triaxial alignment is achieved, the midshaft locking knob 130 is fully tighten.

Figure 22:
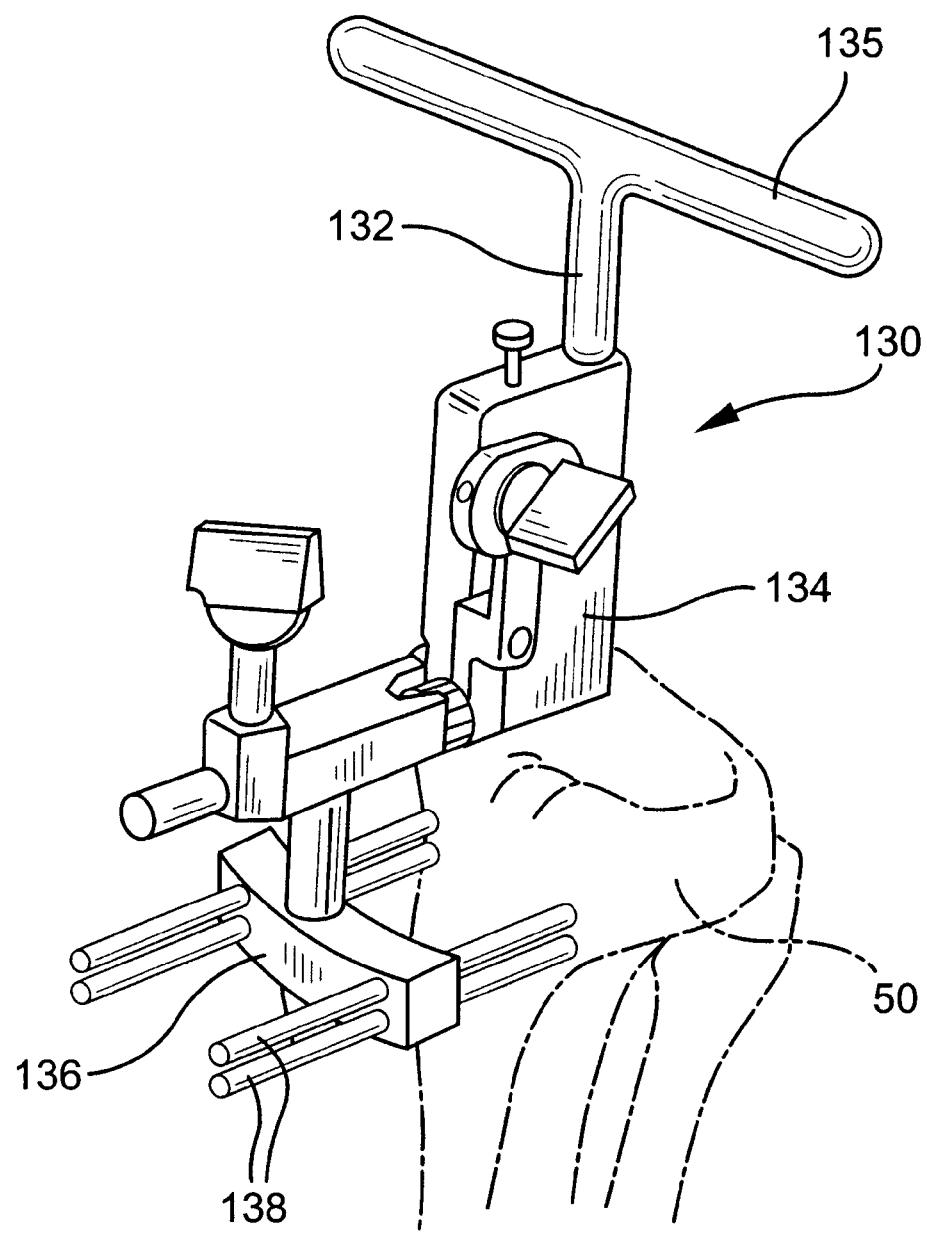
FIG. 22 is an isometric view showing an intramedullary (IM) alignment jig, including a guide block for resecting the proximal tibia.

The second option uses intramedullary referencing. In this procedure, a proximal-distal hole is drilled in the proximal tibia in a location determined by the preoperative X-rays. Referring to FIG. 22, there is shown an IM alignment jig 130 having an IM rod 132. Rod 132 is slowly passed into the drilled hole and into the medullary canal of the tibia, clearing the canal. The rod is then removed using handle 135 and then inserted it into the body 134 of the IM alignment jig 130. The assembly is then reinserted into the canal, and IM rod 132 is passed into the canal until the isthmus is engaged. The tibial cut is then made in a standard manner using a saw guide block 136 which is pinned to the proximal tibia by pins 138.

Resection of the proximal tibia 50 is then completed. A pin puller (not shown) is then used to remove the saw guide block 136. The appropriate'size tibial template 12 of the present invention is then selected and locked onto the tibial alignment handle 56. The appropriate size template will achieve cortical bone support around the periphery of template 12. It is important that the correct size be selected to fully support the tibial component around the periphery with cortical bone.

Tibial alignment handle 56 and guide rod 58 help verify varus/valgus rotation, and flexion/extension alignment. Varus/valgus and flexion/extension alignments are verified with a long alignment rod or pin 58. If a "classical" tibial cut is made, then the neutral tibial alignment hole 59 is used to mount rod 58 on handle 56. The pin 58 should be centered distally over the center of the ankle. The tibial alignment handle 56 and alignment pin 58 may be used to further verify alignment of the template to the tibia in both the A-P and M-L planes.

To determine the correct rotational alignment, the hinged femoral trial component 60 is assembled and inserted onto the already prepared femur. The tibial rotation guide 10 is then assembled to the appropriate size tibial trial template as described above. Hinge 26 of the trial tibial rotation guide-template assembly 10 is then inserted between the condyles having hinge bores 66 of the trial femur 60 and pinned together using a trial axle or pin 64. The resected proximal tibia 50 is then placed against the underside of trial tibial template 12. The handle 56 is removed and the joint is then evaluated to determine the rotation of the tibia and the distal femoral replacement to both determine the internal/external rotation of the tibia and placement of the foot and to optimize the patellar tracking on the distal femoral component and the insertion of the patellar tendon into the tibial tuberosity.

The tibial rotation guide 10 may also be used to help determine femoral rotation when the instrument is used with an oncology system in replacing a distal femur, including part of the long bone of the femur. In this situation, a straight prosthetic portion corresponding to the portion of the femur resected is anchored in the remaining canal of the femur. This straight prosthetic portion in turn is connected to a hinged prosthetic femoral component. In this procedure, prior to resecting the distal femur, a score mark is made on the anterior cortex of the part of the femur which is to remain. This mark is used as an initial rotational alignment guide for the femur prosthesis with the template and hinge portion of the present invention utilized to set the final rotational alignment of the prosthetic femur and long bone replacement.

Once the preferred rotation of the tibia and femur components is obtained, the template 12 is pinned in place against the resected tibia by pins 19 and the rotational alignment mark of the femoral stem is referenced to the marking previously made on the anterior cortex of the femur. The trial axle or hinge pin 64 is then removed and the trial tibial hinge part 14 is disassembled from the tibial template 12, leaving template 12 in place on the resected tibia. If template 12 is overhanging the periphery of tibia 50, the process may be repeated with the next smaller size tibial template 12. Once the proper size template 12 is properly oriented and pinned in place, the remainder of the tibial preparation may proceed.

To begin preparation for the stemmed trial tibial component (not shown), stem punch guide 72 is placed on tibial template 12. The stem punch 70 is inserted into the guide and punch 70 is slowly impacted until it is flush with the guide 72. The plunger 74 is then inserted into the hole of the stem punch 70 and impacted flush. This will position a bone plug (not shown) at the distal tip of the tibial component stem, plugging the tibial medullary canal. The stem punch 70 can then be removed with the impactor/extractor 80.

The rectangular fin/box punch guide 90 is then placed on the tibial template 12. The initial "thin" fin stem punch 92 is inserted into the cutout 91 of the guide and slowly impacted until it is flush with the proximal surface of the guide 90. During insertion, it is important to precisely control the stem punch, maintaining it perpendicular to the resected surface. The fin punch 92 is slowly impacted to allow expansion of the bone.

The final "thick" fin broach 100 is then inserted into the cutout 91 of the guide 90 and slowly impacted until broach 100 is flush with the surface of the guide. During insertion, it is important to precisely control the final stem broach, maintaining it perpendicular to the resected surface. The final fin broach is then removed with the extractor 94.

The box broach 106 is inserted into the cutout 98 of the guide 90 and slowly impacted until it is flush with the surface of the guide. During insertion, it is important to precisely control the box broach, maintaining it perpendicular to the resected surface. The box broach 106 is then removed with the extractor 94.

While in the preferred embodiment the tibial template 12 is rotatably a coupled hinged portion 26 any method of releasably coupling the hinge portion to the tibial template would be acceptable to accomplish the objects of the invention. For example, spring fingers on the hinge portion 26 could be provided to engage corresponding recesses on the tibial templates or vice versa and a release mechanism can be provided.

The tibial template 12 is then removed from tibia 50. The stem reamer (not shown) is then inserted into the center hole of the tibia and slowly turned in a clockwise direction and advanced into the tibia until the circumferential depth mark matching the tibial component stem length is flush with the cut surface of the tibia.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An instrument for setting the rotational alignment of a hinged prosthetic knee implant having a tibial component and a femoral component, the instrument comprising:
    a femoral component having a hinge portion;
    a trial tibial template for engagement with a resected proximal tibia; and
    a trial hinge component having a coupling portion for selectively coupling with said trial tibial template in an orientation corresponding to the tibial portion of the prosthetic knee implant and having a hinge portion for selectively mating with the hinge on said femoral component.

2. The instrument for setting the rotational alignment as set forth in claim 1, wherein the tibial template has a coupling element formed thereon for selectively coupling to said trial hinge component coupling portion.

3. The instrument for setting the rotational alignment as set forth in claim 2, wherein the tibial template has a plate-like body having an opening therethrough and an outer periphery surrounding said opening and a tibia facing surface having said coupling elements formed thereon.

4. The instrument for setting the rotational alignment as set forth in claim 3, wherein the hinge component has a hinge portion and said coupling portion has coupling elements, in the form of projections on said hinge component engagable with recesses which for said coupling elements on said tibial template.

5. The instrument for setting the rotational alignment as set forth in claim 3 further including a shaping tool for mounting on said template and having a portion for forming a recess in the tibia extending through said opening in said template.

6. The instrument for setting the rotational alignment as set forth in claim 5, wherein the recess in the tibia has a shape conforming to a stem portion formed on the tibial portion of the prosthetic knee implant.

7. The instrument for setting the rotational alignment as set forth in claim 1, wherein the trial tibial template is selectively coupled to said trial hinge component by rotational engagement.

8. The instrument for setting the rotational alignment as set forth in claim 7, wherein said trial component includes an anti-rotation element engageable with said template after said selective coupling therewith to prevent the relative rotation between the template and the trial hinge component.

9. A method for determining the rotational alignment of a hinged prosthetic knee implant, comprising:
    providing a femoral component having a hinge portion;
    mounting said femoral component on the femur;
    providing a trial tibial template for engagement with a resected proximal tibia;
    providing a trial hinge component;
    releasably connecting the trial hinge component to both the femoral component hinge portion and the trial tibial template; and
    setting the rotational alignment of the trial tibial template by contacting the resected proximal tibia with said tibial template and orienting the template to optimize the function of the prosthetic knee implant.

10. The method for determining the rotational alignment of a hinged prosthetic knee implant as set forth in claim 9 further comprising pinning the trial tibial template to the resected proximal tibia.

11. The method for determining the rotational alignment of a hinged prosthetic knee implant as set forth in claim 9, wherein the trial hinge component includes a hinge portion for coupling to the hinge portion of the femoral component and coupling elements for selectively coupling to trial tibial template.

12. The method for determining the rotational alignment of a hinged prosthetic knee implant as set forth in claim 10 further comprising resecting the distal femur and mounting the femoral component to the resected distal femur.

13. The method for determining the rotational alignment of a hinged prosthetic knee implant as set forth in claim 9 further comprising pinning the template to the tibia and disconnecting the trial hinge component from the tibial template and the femoral component.

14. The method for determining the rotational alignment of a hinged prosthetic knee implant as set forth in claim 13 further comprising mounting an instrument for forming a recess for a stem of the tibial component on said pinned tibial template.

15. A tibial rotation guide for setting the internal/external rotational alignment of a prosthetic knee implant, said guide comprising:
    a femoral component having a hinge element;
    a tibial template;
    a hinge component; and
    a means for releasably coupling said hinge component to said tibial template and said femoral component.

16. A tibial rotation guide as set forth in claim 15, wherein the tibial template has a coupling element formed thereon for selectively coupling to said trial hinge component coupling portion.

17. A tibial rotation guide as set forth in claim 16, wherein the tibial template has a plate-like body having an opening therethrough and an outer periphery surrounding said opening and a tibia facing surface having said coupling elements formed thereon.

18. A tibial rotation guide as set forth in claim 17, wherein the hinge component has a hinge portion and said coupling portion has coupling elements, in the form of projections on said hinge component engageable with recesses which for said coupling elements on said tibial template.

19. A tibial rotation guide as set forth in claim 17 further including a shaping tool for mounting on said template and having a portion for forming a recess in the tibia extending through said opening in said template.

20. A tibial rotation guide as set forth in claim 15, wherein said trial component includes an anti-rotation element engageable with said template after said selective coupling therewith to prevent the relative rotation between the template and the trial component.

21. A tibial rotation guide as set forth in claim 15, wherein the trial tibial template is selectively coupled to said trial hinge component by rotational engagement.

22. A kit of instruments for setting the rotational alignment of a hinged prosthetic knee implant having a tibial component and a femoral component comprising:
   at least one femoral component having a hinged portion;
   at least one trial tibial template for engaging a resected proximal tibia; and
   a plurality of trial hinged components each having a coupling portion for selectively coupling said trial tibial template in an orientation corresponding to the tibial portion of the prosthetic knee implant and having a hinged portion for selectively mating with the hinge portion on said femoral component.

23. The kit as set forth in claim 22, wherein the hinge portion on each of said plurality of trial hinge components is spaced a different distance from said coupling portion to vary the distance between the trial tibial template and the femoral component.

24. The kit as set forth in claim 23, wherein said at least one trial tibial template has a recess for releasably receiving the coupling element on said trial hinge component.

25. The kit as set forth in claim 22 further including at least one tibial shaping tool.

26. The kit as set forth in claim 25, wherein each trial tibial template includes an opening for receiving shaping tool.

27. The kit as set forth in claim 22 further including at least one hinge pin for engaging the hinge portions of both said femoral component and said trial hinged component.

* * * * *

UNITED STATES PATENT AND TRADEMARK OFFICE
CERTIFICATE OF CORRECTION

PATENT NO.    : 6,645,215 B1
DATED         : November 11, 2003
INVENTOR(S)   : Michael A. McGovern and Richard Lackman It is certified that error appears in the above-identified patent and that said Letters Patent is hereby corrected as shown below:

Column 2,
Line 3, "patients" should read -- patient's --.
Line 52, "being" should read -- is --.

Column 3,
Line 28, "are" should read -- is --.

Column 5,
Line 61, "is" should read -- are --.

Column 7,
Line 43, cancel "it".

Column 9,
Line 57, cancel "which".

Column 10,
Line 33, after "to" insert -- the --.

Column 11,
Line 2, cancel "which".

Column 12,
Line 17, after "receiving" insert -- said --.

Signed and Sealed this

Twentieth Day of January, 2004

JON W. DUDAS
*Acting Director of the United States Patent and Trademark Office*